(12) United States Patent
Chung et al.

(10) Patent No.: US 8,697,389 B2
(45) Date of Patent: *Apr. 15, 2014

(54) CELL LABELING AND IMAGING USING MULTIFUNCTIONAL PERFLUOROCARBON NANOEMULSION

(75) Inventors: Bong Hyun Chung, Daejeon (KR); Yong Taik Lim, Daejeon (KR)

(73) Assignee: Korea Research Institute of Bioscience And Biotechnology, Daejeon (KR)

( * ) Notice: Subject to any disclaimer, the term of this patent is extended or adjusted under 35 U.S.C. 154(b) by 428 days.

This patent is subject to a terminal disclaimer.

(21) Appl. No.: 12/937,875

(22) PCT Filed: Mar. 24, 2009

(86) PCT No.: PCT/KR2009/001488
§ 371 (c)(1),
(2), (4) Date: Nov. 11, 2010

(87) PCT Pub. No.: WO2009/128610
PCT Pub. Date: Oct. 22, 2009

(65) Prior Publication Data
US 2012/0088261 A1    Apr. 12, 2012

(30) Foreign Application Priority Data
Apr. 17, 2008  (KR) .................. 10-2008-0035673

(51) Int. Cl.
*C12Q 1/02*    (2006.01)
(52) U.S. Cl.
USPC ............ 435/29; 435/34; 435/325; 435/372.1; 435/372.3
(58) Field of Classification Search
USPC .................. 435/29, 34, 325, 372.1, 372.3
See application file for complete search history.

(56) References Cited

U.S. PATENT DOCUMENTS

| | | | | |
|---|---|---|---|---|
| 5,958,371 A | * | 9/1999 | Lanza et al. | 424/1.21 |
| 2006/0083781 A1 | * | 4/2006 | Shastri et al. | 424/450 |
| 2007/0253910 A1 | * | 11/2007 | Ahrens et al. | 424/9.34 |
| 2010/0233094 A1 | * | 9/2010 | Chung et al. | 424/9.32 |

FOREIGN PATENT DOCUMENTS

| | | |
|---|---|---|
| WO | 2005/014051 A1 | 2/2005 |
| WO | 2006/064451 A2 | 6/2006 |
| WO | 2006/084382 A1 | 8/2006 |

OTHER PUBLICATIONS

Ikushima et al. Studies in Surface Science and Catalysis (2006) 159: 729-732.*
B.O. Dabbousi, et al., (CdSe)ZnS Core-Shell Quantum Dots . . . , J. Phys. Chem B, 101, pp. 9463-9475, 1997.
Trung D. Tran, et al., Clinical Applications of Perfluorocarbon Nanoparticles . . . , International Journal of Nanomedicine, pp. 515-526, 2007.
H. Duan and S. Nie, "Cell-penetrating quantum dots based on multivalent and endosome-disrupting surface coatings.", J. Am. Chern. Soc., vol. 129(11):3333-3338, Published online, Feb. 24, 2007.
G. Hu, et al., "Imaging of Vx-2 rabbit tumors with a V B 3-intergrin-targeted in nanoparticles.", International Journal of Cancer, vol. 120(9):1951-1957, Published online, Feb. 2, 2007.

* cited by examiner

*Primary Examiner* — Susan Hanley
(74) *Attorney, Agent, or Firm* — Lucas & Mercanti, LLP (57) ABSTRACT

The present invention relates to cell labeling and imaging using a multifunctional perfluorocarbon (PFC) nanoemulsion. In particular, the perfluorocarbon nanoemulsion containing optical nanoparticle is provided with both optical characteristics and $^{19}$F magnetic resonance characteristics, thus can be used for magnetic resonance imaging (MRI) and optical imaging (OI) simultaneously. Cell labeling and imaging using the perfluorocarbon nanoemulsion containing quantum dot nanoparticle exerted no effect on cell viability. Therefore, perfluorocarbon nanoemulsion can be applied to methods for multifunctional and effectively cell labeling and imaging.

13 Claims, 11 Drawing Sheets

CELL LABELING AND IMAGING USING MULTIFUNCTIONAL PERFLUOROCARBON NANOEMULSION

CROSS-REFERENCE TO RELATED APPLICATIONS

This application is a 371 of PCT/KR2009/001488, filed on Mar. 24, 2009, which claims the benefit of Korean Patent Application No. 10-2008-0035673, filed on Apr. 17, 2008, the contents of each of which are incorporated herein by reference.

BACKGROUND OF THE INVENTION

1. Field of the Invention

The present invention relates to a multimodal bioimaging, more particularly, to a method for cell labeling and imaging using perfluorocarbon (PFC) nanoemulsion containing optical nanoparticle.

2. Description of the Related Art

Labeling cells with nanoparticle having optical and magnetic properties is widely used in the area of cell imaging and disease treatment. The technology of internalizing nanoparticles into the cells is critical for cell labeling. The interaction between nanoparticle and cells depend on the cell surface characteristics, therefore, the technology for reforming the surface of nanoparticle is very important in cell labeling. In general, internalizing functional nanoparticles into cells is performed by coating the nanoparticle surface with signaling peptides that are related to transfection, which can induce an interaction between the cells and the nanoparticle. Phagocytic cells, such as macrophages show high interaction with nanoparticles without any specific surface modifications, however there is difficulty in transporting nanoparticles into non-phagocytic cells, such as stem cells and NK cells. For non-phagocytic cell labeling, electroporation or nucleofection techniques, which transport nanoparticle or genes into cells using mechanical forces, are widely used. The technology for labeling cells with imaging agent is critical when monitoring the cells in the field of using stem cells and immune cells for treating diseases, such as cancers.

Hematopoietic stem cells are one of adult human stem cells with the ability to differentiate into blood forming cells (red blood cell, white blood cell, platelets and lymphocytes). Hematopoietic cells in the bone marrow continuously self-renew into cells forming the immune system. One of the cells of the immune system is Natural Killer cell (NK cell), which can nonspecifically kill cancer cells. The cytotoxicity of NK cell, such as lymphokine activated killer cell (LAK) and tumor infiltration lymphocytes (TIL) can be used to treat solid tumor or used for immune therapy by donor lymphocyte infusion method (Itoh, K, et al., *J. Immunol.*, 36: 3910-3915, 1986; Bordignon C. et al., *Haematologica*, 84: 1110-1149, 1999) which can be used as a new cell treatment method to prevent the immune rejection response after stem cell transplant or organ transplant. In addition, depletion of NK cell differentiation and activity have been reported to be involved in various disease such as breast cancer (Konjevi G, et al., *Breast Cancer Res. Treat.*, 66: 255-263, 2001), subcutaneous melanoma (Ryuke Y, et al., *Melanoma Res.*, 13: 349-356, 2003) and lung cancer (Villegas F R, et al., *Lung Cancer*, 35: 23-8, 2002), therefore suggesting a possible NK cell treatment for treating these diseases.

However, due to its difficulty in introducing image contrast reagent into NK cells or labeling the NK cells, there is no report on using a molecular imaging agent for imaging or labeling NK cells to treat disease (Giovanni Lucignani et al., *Trends Biotechnol.*, 24: 410-418, 2006). Recently, a method of introducing image contrast reagents into genetically modified NK cells expressing HER-2/neu receptor using lipofection and electroporation method (*Eur Radiol.*, 15: 4-13, 2005) and an indirect treatment method by expressing reporter gene using retroviral vector (Edinger, M. et al., *Blood*, 101: 640-648, 2003) has been introduced, but had the disadvantage of affecting the cell activity.

Perfluorocarbon (PFC) is widely used in various areas in industry due to its low viscosity, low dielectric constant, high vapor pressure, high compressibility and high gas solubility. When applied to clinical use, perfluorocarbon has an advantage of having high density, antifriction properties and magnetic susceptibility values close to water. In addition, high dose of perfluorocarbon is safe in human body and pure fluorocarbon within certain molecular weight range (460-520 Da) is non-toxic, non-carcinogenic, non mutagenic and non-teratogenic and does not trigger immune responses. Perfluorocarbon is widely applied in liquid ventilation, oxygen delivery and imaging due to its physiological inactivity and biocompatibility (Marie Pierre Krafft, *Advanced Drug Delivery Reviews*, 47:209, 2001; Gregory M., et al., *Current Topics in Developmental Biology*, 70:57, 2005).

The gas phase PFC which forms lipid coated low density micro-bubbles have been widely studied as an ultrasound imaging agent and are being used commercially. PFC micro-bubbles have been studied as transporting bioactive materials to specific local regions and for the treatment purpose due to its cavitation by ultrasound energy. The study is focused in diagnostic imaging of cardiovascular related cancers and improving treatment by drug delivery (Evan C et al., *Advanced drug delivery Reviews*, 56: 1291, 2004).

Perfluorocarbon (PFC) is an excellent contrast material for MRI, the PFC and derivatives to have been actively studied in $^{19}F$ MRI fields. As compared with conventional $^{1}H$ MRI imaging agents, $^{19}F$ has an almost identical gyromagnetic ratio to protons, a spin ½ nucleus and 100% of natural isotope abundance. It has an advantage of not being a source of a man-made pollution and has a background concentration which is same as the environmental concentration found in nature.

PFC emulsion nanoparticle may be functionalized as a MRI molecular imaging agents by bonding paramagnetic chelates and homing ligands onto an external phospholipid monolayer in MRI field, and many studies of the PFC emulsion nanoparticles have been conducted as drug delivery vectors including bioactive agents (US 2004/0115192 A1; U.S. Pat. No. 6,676,963 B1; US 2003/0086867; US 2003/0215392 A1; US 2004/0248856 A1). In the MRI, the nuclei are dephased and then rearranged in the direction of a magnetic field. At this time, the process of supplying energy to the lattice of the nuclei to reach a thermal equilibrium is referred to as T1. The PFC emulsion nanoparticles are used as T1-weighted ultraparamagnetic imaging agents reflected in particulate or molecular relaxivity. For the imaging agents to have maximum relaxivity, all the paramagnetic materials used as the imaging agents are necessarily in an external aqueous phase. In 1.5 T, the molecular relaxivity of the PFC nanoparticles depends on lipophilic chelation and has a value of 1,000,000 to 2,000,000 mMs$^{-1}$ (Flacke et al, Circulation, 104:1280, 2001; Winter et al, Magn. Reson. med., 50:411, 2003).

Biotin ligand sandwiched with biotin treated nanoparticle by streptavidin-biotin interaction for molecular imaging, fibrin imaging which can detect the blood clots by direct covalent bonding of ligand and the monoclonal antibody targeting of molecular epitopes, this research was performed on imaging of angiogenesis in cancer and imaging of early atherosclerosis to detect the low expression level of $\alpha_v\beta_3$ integrin and for anti-angiogenesis treatment (U.S. Pat. No. 5,690,907; US 2004/0058951 A1; US 2006/0147380 A1).

The PFC emulsion nanoparticle currently used for molecular imaging are using the MR characteristic of $^{19}F$ or loading contrast reagent for $^1H$ MR by adding a reagent that can chelate gadolinium (Gd) that can be used as the T1 contrast agent that envelops the lipid layer of PFC emulsion nanoparticle.

The present inventors have discovered that perfluorocarbon nanoemulsion containing optical nanoparticle can label various cell types from phagocytic cells that are readily labeled, to NK cells that are difficult to be labeled. The labeling exerted no effect on cell viability and function of the NK cells. As a result, the inventors have developed multifunctional cell labeling and imaging techniques that can be used in magnetic resonance imaging (MRI) and optical imaging (OI) simultaneously, thus completed the present invention.

SUMMARY OF THE INVENTION

One object of the present invention is to provide cell labeling and imaging agent including perfluorocarbon nanoemulsion containing optical nanoparticle, a method for labeling and imaging cell using the cell labeling and imaging agent, and a use of perfluorocarbon nanoemulsion containing optical nanoparticle in the manufacture of cell labeling and imaging agent.

In order to achieve the above objective, the present invention provides cell labeling and imaging agent including perfluorocarbon nanoemulsion that contains optical nanoparticle.

The present invention also provides a method for labeling and imaging cell, including treating cells with cell labeling and imaging agent including perfluorocarbon nanoemulsion containing optical nanoparticles; and imaging the cells.

In addition, the present invention provides a use of perfluorocarbon nanoemulsion containing optical nanoparticle in the manufacture of cell labeling and imaging agent.

DETAILED DESCRIPTION OF THE INVENTION

Hereinafter, the present invention will be described in detail.

The present invention provides cell labeling and imaging agent including perfluorocarbon nanoemulsion containing optical nanoparticle.

Figure 1:
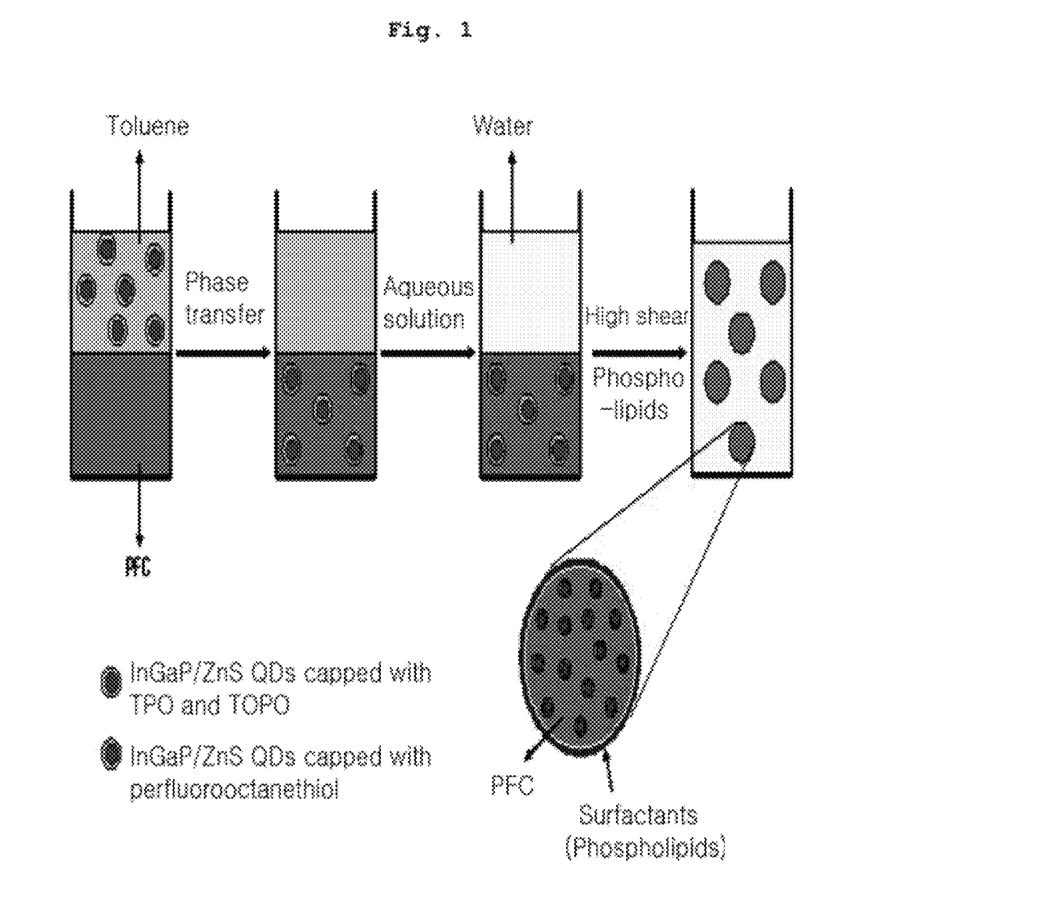
FIG. 1 is a diagram illustrating the process of preparing Perfluorocarbon (PFC) nanoemulsion containing optical nanoparticle with a lipid layer coated on the surface.
Figure 2:
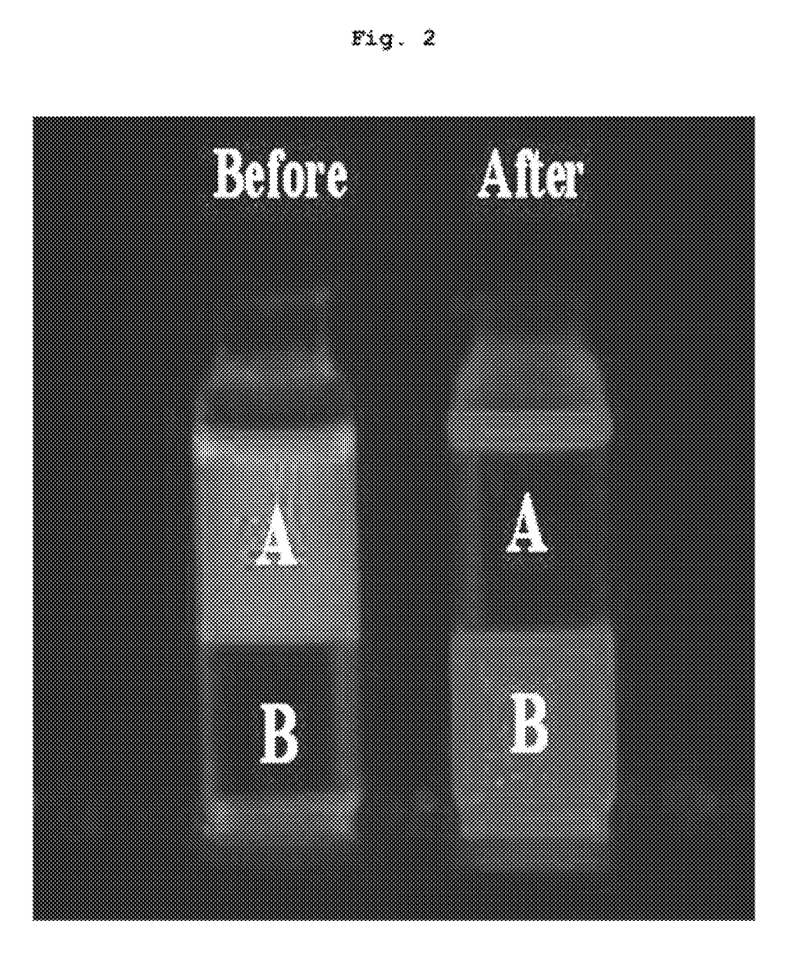
FIG. 2 is a fluorescent image showing optical nanoparticle dispersed with toluene (A), then being phase transferred into perfluorocarbon layer (B).

Preferably, the perfluorocarbon nanoemulsion containing optical nanoparticle may be prepared by the following, but not limited to, method including:

1) Reforming the surface of hydrocarbon coated quantum dot nanoparticle by coating with perfluorocarbon; and 2) Dispersing the surface reformed nanoparticle in step 1) into perfluorocarbon solution; and 3) Emulsifying the liquid in step 2) (see FIG. 1 and FIG. 2).

According to above method, the quantum dot nanoparticle in step 1) may preferably consist of two or more compounds selected from the group consisting of, but not limited to, II-VI or III-V compounds in the periodic table. Preferably, the optical nanoparticle may be selected from the group consisting of a single core or a core/shell. More preferably, the optical nanoparticle may be selected from the group consisting of, but not limited to, CdSe, CdSe/ZnS, CdTe/CdS, CdTe/CdTe, ZnSe/ZnS, ZnTe/ZnSe, PbSe, PbS, InAs, InP, InGaP, InGaP/ZnS and HgTe.

Preferably, the optical nanoparticle may be selected from the group consisting of quantum dot nanoparticles, organic fluorescent dyes and metal nanoparticles, but not limited thereto.

In the method, the perfluorocarbon in step 1) for surface reforming preferably includes a perfluorochemical having one end group selected from the group consisting of thiol, phosphine and phosphine oxide, or an amphiphilic fluorinated hydrocarbon. More preferably, the perfluorocarbon for surface reforming includes one selected from the group consisting of, but not limited to, perfluorinated alcohol phosphate ester and its salt, perfluorinated sulfonamide alcohol phosphate ester and its salt, perfluorinated alkyl sulfonamide alkylene quaternary ammonium salt, N,N-(carboxyl-substituted lower alkyl) perfluorinated alkyl sulfonamide, and a compound thereto.

The perfluorinated alcohol phosphate ester may include, but not limited to, a free acid of mono or bis(1H, 1H, 2H, 2H-perfluoroalkyl)phosphate derived diethanolamine salt.

The perfluorinated sulfonamide alcohol phosphate ester may be one selected from the group consisting of, but not limited to, perfluoro-n-octyl-N-ethysulfonamidoethyl phosphate, bis(perfluoro-n-octyl-N-ethylsulfonamidoethyl) phosphate, ammonium salt of bis(perfluoro-n-octyl-N-ethylsulfonamidoethyl) phosphate, bis(perfluorodecyl-N-ethylsulfonamidoethyl phosphate and bis(perfluorohexy-N-ethylsulfonamidoethyl) phosphate.

In the method, the perfluorocarbon used to disperse the optical nanoparticle coated with perfluorocarbon molecule in step 2) is preferably one selected from the group consisting of, but not limited to, perfluorotributylamine (FC47), perfluorodecalin (PP5), perfluoromethyldecalin (PP9), perfluorooctylbromide, perfluorotetrahydrofuran (FC80), perfluoroether (PID) $[(CF_3)_2CFOCF_2(CF_2)_2CF_2OCF(CF_3)_2]$, perfluoroether (PIID) $[(CF_3)_2CFOCF_2(CF_2)_6CF_2OCF(CF_3)_2]$, perfluoroetherpolymer (Fomblin Y/01), perfluorododecane, perfluorobicyclo[4.3.0]nonane, perfluorotritrimethylbicyclohexane, perfluorotripropylamine, perfluoroisopropylcyclohexane, perfluoroendotetrahydrodicyclopentadiene, perfluoroadamantane, perfluoroexotetrahydrodicyclopentadiene, perfluorobicyclo[5.3.0]decane, perfluorotetramethylcyclohexane, perfluoro-1-methyl-4-isopropylcyclohexane, perfluoro-n-butylcyclohexane, perfluorodimethylbicyclo[3.3.1]nonane, perfluoro-1-methyladamantane, perfluoro-1-methyl-4-t-butylcyclohexane, perfluorodecahydroacenapthane, perfluorotrimethylbicyclo[3.3.1]nonane, perfluoro-nundecane, perfluorotetradecahydrophenanthrene, perfluoro-1,3,5,7-tetramethyladamantane, perfluorododecahydrofluorene, perfluoro-1-3-dimethyladamantane, perfluoro-n-octylcyclohexane, perfluoro-7-methyl bicyclo[4.3.0]nonane, perfluoro-p-diisopropylcyclohexane, perfluoro-m-diisopropylcyclohexane, perfluoro-4-methyloctahydroquinolidizine, perfluoro-N-methyldecahydroquinoline, F-methyl-1-oxadecalin, perfluorooctahydroquinolidizine, perfluoro 5,6-dihydro-5-decene, perfluoro-4,5-dihydro-4-octene, perfluorodichlorooctane, perfluorobischlorobutyl ether, perfluorooctane, perfluorodichlorooctane, perfluoro-n-octyl bromide, perfluoroheptane, perfluorodecane, perfluorocyclohexane, perfluoromorpholine, perfluorotripropylamine, perfluorotributylamine, perfluorodimethylcyclohexane, perfluorotrimethylcyclohexane, perfluorodicyclohexyl ether, and perfluoro-n-butyltetrahydrofuran, and structurally similar compounds.

In the method, the emulsification in step 3) may be performed using one or more selected from the group consisting of, but not limited to, homogenizer, sonication and high shear force.

The perfluorocarbon nanoemulsion containing optical nanoparticle may be encapsulated by forming, but not limited to, an external layer using a lipid/surfactant.

The lipid containing the external layer which coats the perfluorocarbon nanoemulsion may be selected from the group consisting of natural or synthetic phospholipid, fatty acids, cholesterols, lysolipids, sphingomyelins, tocopherols, glucolipid, stearylarnines, cardiolipins, plasmalogens, lipid with ether or ester linked fatty acids, and polymerized lipids.

The surfactant containing the external layer which coats the perfluorocarbon nanoemulsion may be selected from the group consisting of, but not limited to, anionic surfactants, cationic surfactants, nonionic surfactants and an amphoteric surfactants.

Preferably, the surfactant is one or more selected from the group consisting of, but not limited to, an anionic surfactant, a cationic surfactant, a nonionic surfactant and an amphoteric surfactant, which are being used commercially. More preferably, the surfactant is one or more selected from the group consisting of Pluronic™ F-68, Hamposyl™ L30, sodium dodecyl sulfate, Aerosol™ 413, Aerosol™ 200, Lipoproteol™ LCO, Standapol™ LCO, Standapol™ SH 135, Fizul™ 10-127, Cyclopol™ SBFA 30, Deriphat™ 170, Lonzaine™ JS, Niranol™ C2N-SF, Amphoterge™ W2, Amphoterge™ 2WAS, Pluronic™ F-68, Pluronic™ F-127, Brij™ 35, Triton™ X-100, Brij™ 52, Span™ 20, Generol™ 122 ES, Triton™ N-42, Triton™ N-101, Triton™ X-405, Tween™ 80, Tween™ 85 and Brij™56.

The perfluorocarbon nanoemulsion containing optical nanoparticle may attach or conjugate aptamers or nucleic acids on nanoparticle surface using cationic lipids.

The cationic lipid may be one selected from the group consisting of, but not limited to, N-[1-(2,3-dioleoyloxy)propyl]-N,N,N-trimethylammonium chloride (DOTMA), 1,2-dioleoyloxy-3-(trimethylammonio)propane (DOTAP), 1,2-dioleoyl-3-(4'-trimethyl-ammonio)butanoyl-sn-glycerol (DOTB), 1,2-diacyl-3-dimethylammonium-propane (DAP), 1,2-diacyl-3-trimethylammonium-propane (TAP), 1,2-diacyl-sn-glycerol-3-ethylphosphocholine, 3β-(N',N'-dimethylaminoethane)-carbamolcholestrol-HCl, DC-Cholesterol, and dimethyldioctadecylammonium bromide (DDAB).

Preferably, the cells that can be applied to cell labeling and imaging may be one selected from the group consisting of, but not limited to, cancer cells, stem cells, B cells, T cells, NK cells, dendritic cells and phagocytic cells, more preferably phagocytic cells, dendritic cells and NK cells. Cells with or without phagocytosis functions are all included.

The NK cells may be NK cells isolated from, but not limited to, hematopoietic stem cells, blood, spleen and liver, or the above NK cells genetically modified.

The perfluorocarbon nanoemulsion containing optical nanoparticle is provided with both optical properties and $^{19}F$ magnetic resonance properties, thus can be used in magnetic resonance imaging (MRI) and optical imaging (OI) simultaneously.

Figure 3:
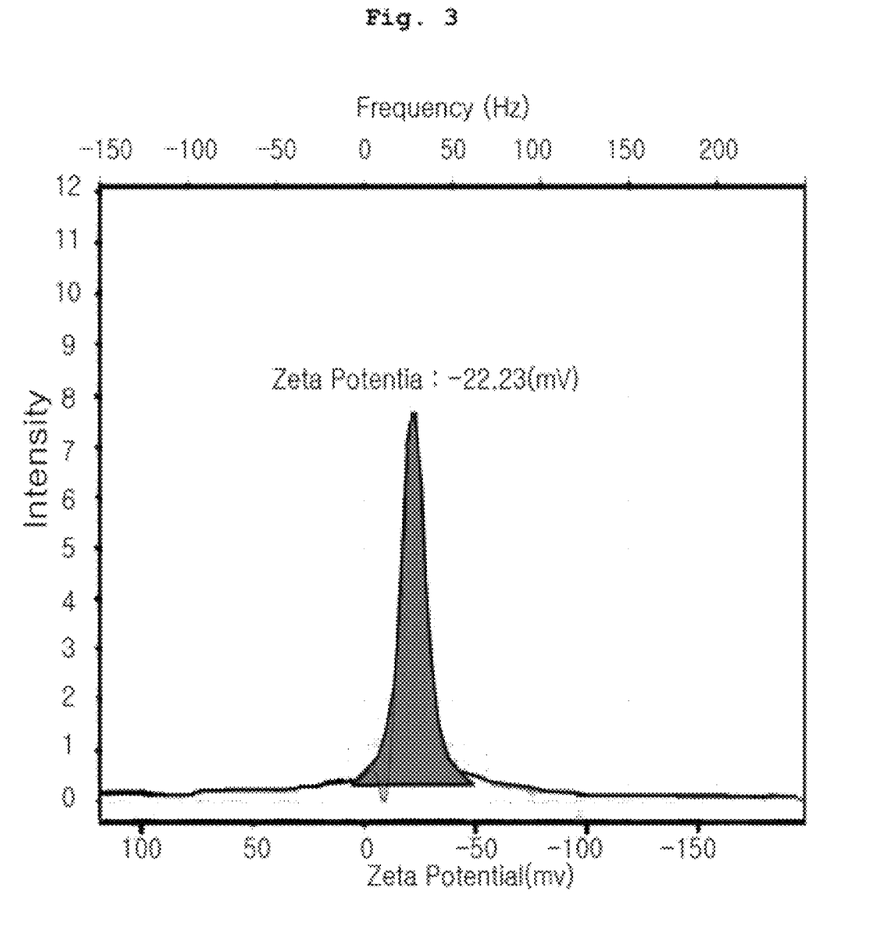
FIG. 3 is a graph showing the zeta-potential of perfluorocarbon nanoemulsion containing optical nanoparticle.
Figure 4:
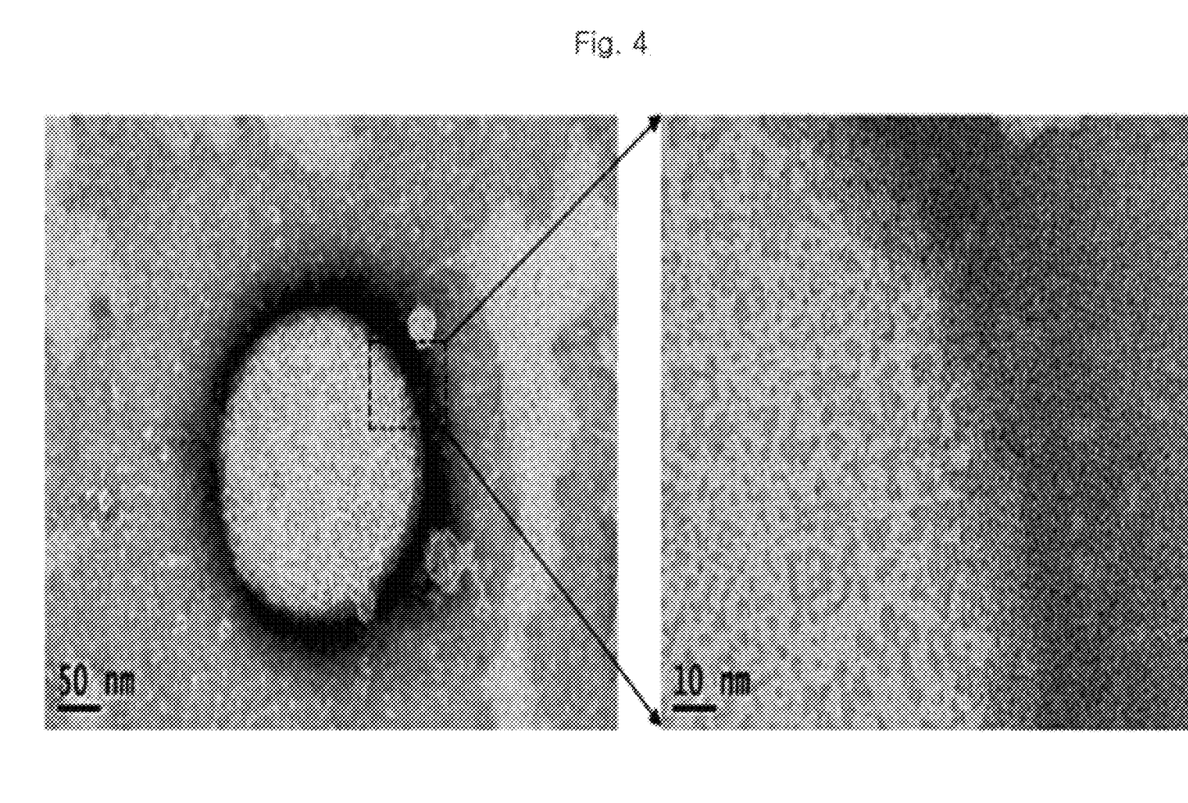
FIG. 4 is Transmission Electron Microscopy (TEM) image of perfluorocarbon nanoemulsion containing optical nanoparticle.
Figure 5:
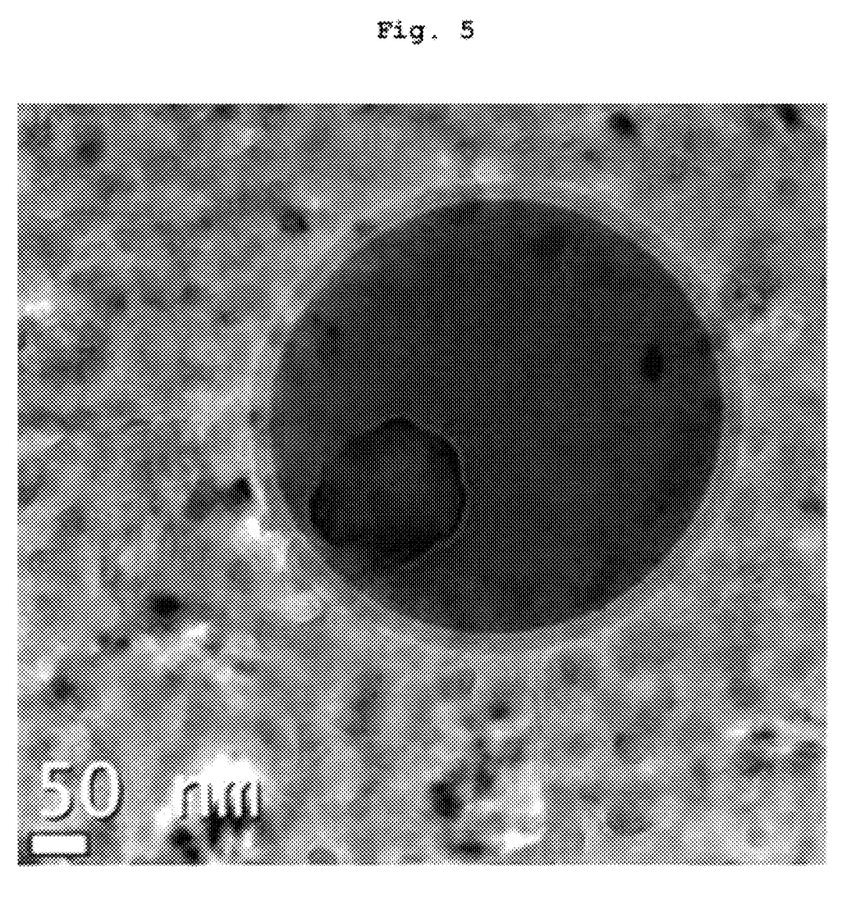
FIG. 5 is a Cryo-TEM image of perfluorocarbon nanoemulsion containing optical nanoparticle.
Figure 6:
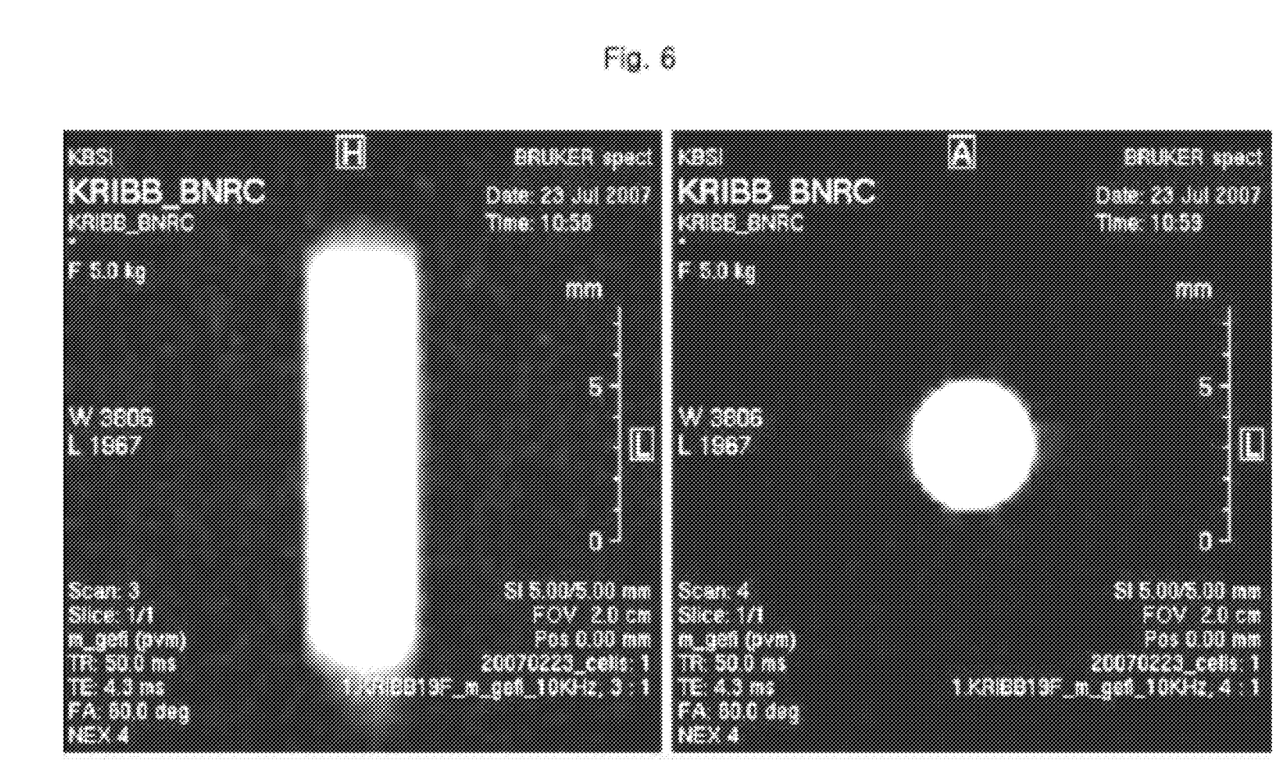
FIG. 6 is a $^{19}$F MRI (Magnetic resonance imaging) image of perfluorocarbon nanoemulsion containing optical nanoparticle.

To investigate the characteristics of perfluorocarbon nanoemulsion containing optical nanoparticle, the present inventors analyzed its electrical and morphological properties. The zeta potential value measured by Electrophoretic light scattering was 22.2 mV (see FIG. 3) as shown in FIG. 3. The morphology of the nanoparticle observed using electron microscope and $^{19}F$ MRI showed that nanoparticle had similar size and morphological properties as shown in FIGS. 4 to 6. (See FIGS. 4, 5, and 6).

To investigate whether perfluorocarbon nanoemulsion containing optical nanoparticle can be used in magnetic resonance imaging (MRI) and optical imaging (OI) simultaneously, phagocytic cells, dendritic cells and NK cells were analyzed using Deltavision RT image system and 4.5 T MRI scanner. The results shown in FIGS. 6 to 9 indicated that phagocytic cells, dendritic cells and NK cells were labeled with perfluorocarbon nanoemulsion containing optical nanoparticle. Therefore, the disclosed perfluorocarbon nanoemulsion containing optical nanoparticle showed the ability to perform magnetic resonance imaging (MRI) and optical imaging (OI) analysis simultaneously.

Figure 11:
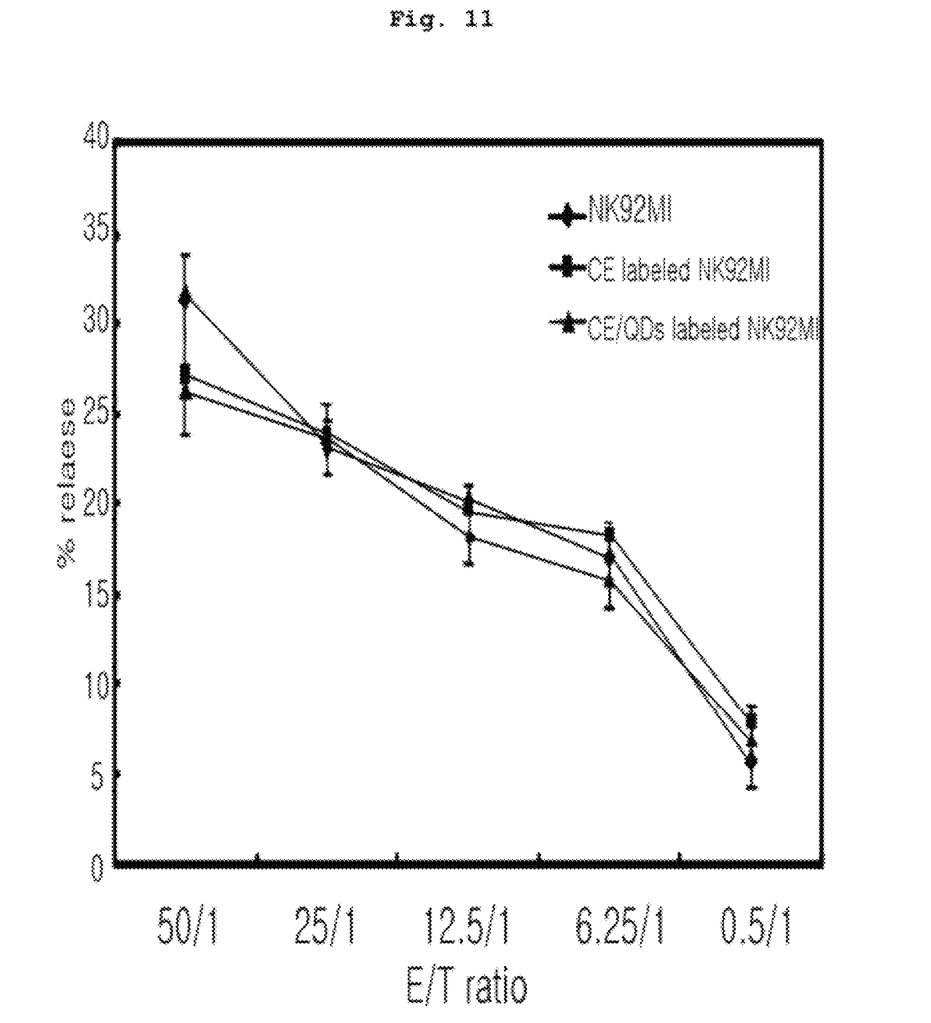
FIG. 11 is a graph showing the cell viability of NK cells labeled with various concentrations of perfluorocarbon nanoemulsion containing optical nanoparticle.

In order to investigate the effect of labeling with perfluorocarbon nanoemulsion containing optical nanoparticle on NK cell viability, NK cells were incubated with perfluorocarbon nanoemulsion containing optical nanoparticle and the cell viability was analyzed by PI staining method. The result in FIG. 11 showed no significant difference in cell viability when compared with the no emulsion treated control group (FIG. 11). In conclusion, the perfluorocarbon nanoemulsion containing optical nanoparticle showed no effect on cell viability (see FIG. 11).

The present invention also provides 1) a method for labeling and imaging NK cells, including treating cells with imaging agent including perfluorocarbon nanoemusion containing optical nanoparticles; and imaging the cells.

Preferably, the cells that can be used for cell labeling and imaging may be one selected from the group consisting of, but not limited to, cancer cells, stem cells, B cells, T cells, NK cells, dendritic cells and phagocytic cells, more preferably phagocytic cells, dendritic cells and NK cells. Cells with or without phagocytosis functions are all included.

The NK cells may be NK cells isolated from, but not limited to, hematopoietic stem cells, blood, spleen and liver, or the above NK cells genetically modified.

The cells are treated with nanoemulsion and incubated for 3 to 24 hrs and the nanoemulsion was internalized into the cells, therefore enabling the cells to be labeled.

The cell labeling and imaging may use, but not limited to, perfluorocarbon nanoemulsion containing optical nanoparticle fixed with biomolecules.

The cell labeling and imaging method may be performed by using cell labeling and imaging reagents alone, or combined with a chemical induction of transfection, or combined with a mechanical induction of transfection, but not limited thereto.

The chemical transfection may use, but not limited to, a cationic agent.

The mechanical transfection may use, but not limited to, electroporation or magnetoporation.

In addition, the present invention provides a use of perfluorocarbon nanoemulsion containing optical nanoparticle in the manufacture of a cell labeling and imaging agent.

Preferably, the perfluorocarbon nanoemulsion containing optical nanoparticle may be prepared by the following method comprising, reforming the surface of hydrocarbon coated quantum dot nanoparticle by coating with perfluorocarbon; dispersing the surface reformed nanoparticle into perfluorocarbon solution; and emulsifying the dispersed liquid. However the present invention is not limited thereto.

The perfluorocarbon nanoemulsion containing optical nanoparticle may form an external layer using, but not limited to, a lipid/surfactant.

The perfluorocarbon nanoemulsion containing optical nanoparticle may attach or conjugate aptamers or nucleic acids on nanoparticle surface using cationic lipids.

Preferably, the cells that can be applied to cell labeling and imaging may be ones selected from the group consisting of, but not limited to, cancer cells, stem cells, B cells, T cells, NK cells, dendritic cells and phagocytic cells, more preferably phagocytic cells, dendritic cells and NK cells. Cells with or without phagocytosis functions are all included.

The perfluorocarbon nanoemulsion containing optical nanoparticle is provided with both optical properties and $^{19}$F magnetic resonance properties, which can be used for performing magnetic resonance imaging (MRI) and optical imaging (OI), simultaneously.

The perfluorocarbon nanoemulsion containing optical nanoparticle showed similar morphological and electrical properties. They were detected by both magnetic resonance imaging (MRI) and optical imaging (01), and did no affect the NK cell viability when the cells were labeled. Therefore, perfluorocarbon nanoemulsion containing optical nanoparticle can be applied to manufacturing a composition for labeling and imaging various cells, including NK cells.

DESCRIPTION OF THE PREFERRED EMBODIMENTS

Features and advantages of the present invention will be more clearly understood by the following detailed description of the present preferred embodiments by reference to the accompanying drawings. It is first noted that terms or words used herein should be construed as meanings or concepts corresponding with the technical spirit of the present invention, based on the principle that the inventor can appropriately define the concepts of the terms to best describe his own invention. Also, it should be understood that detailed descriptions of well-known functions and structures related to the present invention will be omitted so as not to unnecessarily obscure the important point of the present invention.

The present invention will now be described in further detail by examples. It would be obvious to those skilled in the art that these examples are intended to be more concretely illustrative and the scope of the present invention as set forth in the appended claims is not limited to or by the examples.

Example 1

Surface Reformation of Optical Nanoparticle Using Perfluorocarbon

The present inventors added 50 µl of optical nanoparticle (CdSe/ZnS [520 nm], InGaP/ZnS [670 nm] 1.4 mg/ml in toluene) (Evident Tech Co, USA) into methanol to a final volume of 8 ml. Four ml of perfluorocarbon was added to the mixture. After phase separation, 0.5 ml of 1H,1H,2H,2H-Perfluorodecanethiol (ALDRICH, USA) was slowly added in drop wise. The phase separated solution was vigorously stirred until the quantum dot has moved into two layers, the perfluorocarbon layer and the other, which is the middle layer of methanol and perfluorocarbon (FIG. 2). After the reaction, the supernatant (methanol layer) was decanted and an excessive amount of methanol was added then mixed to remove unreacted 1H, 1H, 2H, 2H-Perfluorodecanethiol. This procedure was repeated for three times.

Example 2

Preparation of Nanoemulsion Containing Optical Nanoparticle

The inventors prepared 2.0 w/v of surfactant commixture, which forms the lipid layer that surrounds the liquid perfluorocarbon containing optical nanoparticle as referred in <Example 1>. The surfactant commixture was prepared with 64 mol % lecithin (Sigma Chemical Co., USA), 35 mol % cholesterol (Sigma Chemical Co., USA) and 1 mol % DPPE-PEG 2000(Avanti Polar Lipids, Inc., Alabaster, Ala., USA).The surfactant commixture was dissolved in chloroform, then the solvent was evaporated under reduced pressure, dried in a 50° C. vacuum oven overnight to form a thin lipid film. The lipid film was dispersed into tertiary distilled water by sonication, resulting in a liposome suspension.

Forty % v/v of perfluorocarbon containing optical nanoparticle, 1.7% w/v glycerin, 2.0% w/v of above prepared surfactant commixture and rest filled with distilled water were mixed for 30 sec by using homogenizer (Power Gen 1000, Fischer Scientific, USA). The mixture was transferred to a Microfluidics emulsifier (Microfluidics Co.) and processed at 2000 PSI for 4 min. The perfluorocarbon nanoemulsion containing optical nanoparticle were vialed, sealed and stored at 4° C.

Example 3

Characterization of Perfluorocarbon Nanoemulsion Containing Optical Nanoparticle To investigate the electrical properties of the nanoparticle surface in perfluorocarbon nanoemulsion containing optical nanoparticle, the inventors analyzed the zeta potential using Electrophoretic light scattering (ELS 8000, Otsuka Electronics). As a result, FIG. 3 showed that the zeta potential value was 22.2 mv (FIG. 3).

The nanoparticle from perfluorocarbon nanoemulsion containing optical nanoparticle were stained with 1% phosphotungstic acid and then place on a formvar-coated grid. The morphology of the nanoparticle were observed using a 200-kV Field Emission Transmission Electron Microscope (JEM-2100F, JEOL, LTD)(FIG. 4). Also, the perfluorocarbon nanoemulsion containing optical nanoparticle were prepared to form a thin film on a carbon coated grid. The grid was immersed in ethanol and stored in liquid nitrogen. The frozen sample was transferred to a GATAN model 630 cryotransfer, and the images were collected with Multiscan 600W CCD camera (Gatan, Inc., Warrendale, Pa.) at 120 kV (FIG. 5). In addition, the $^{19}$F MRI image of perfluorocarbon nanoemulsion containing optical nanoparticle was measured with a 4.5 T MRI scanner (Bruker, Germany) (FIG. 6). The results from FIGS. 4 to 6 showed that nanoparticle had similar size and morphological properties.

Example 4

Analysis of Cell Labeling

Figure 7:
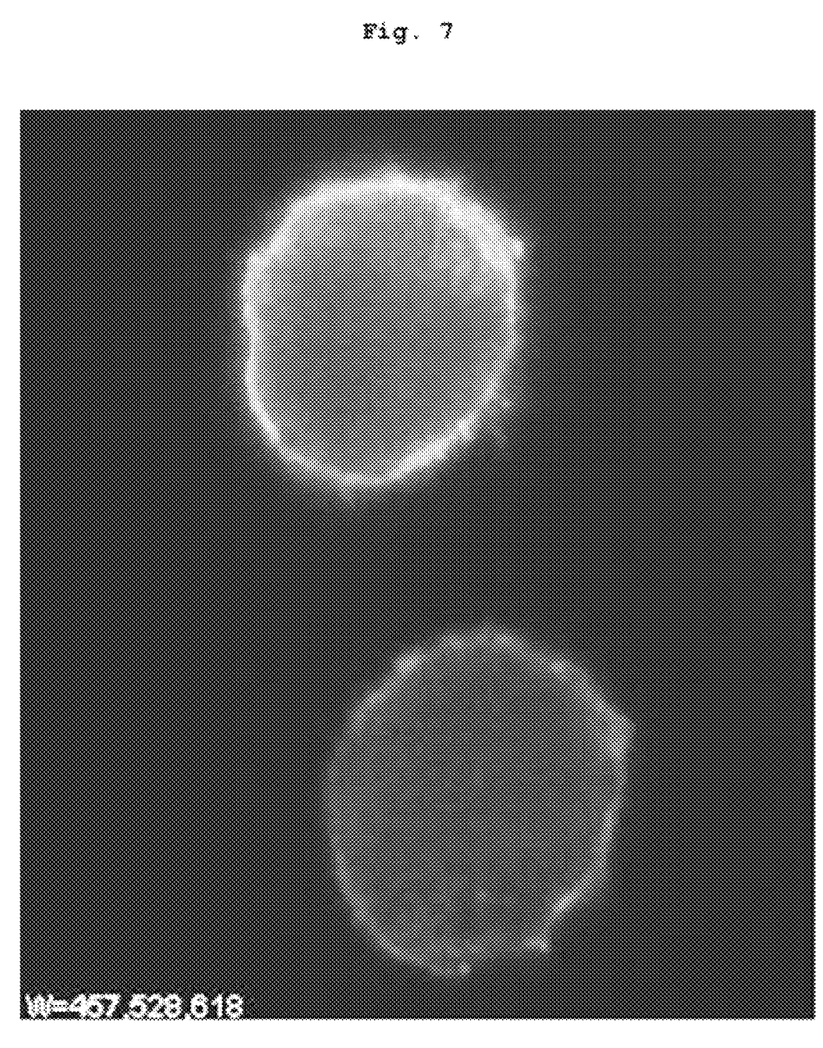
FIG. 7 is a fluorescent microscope image of NK cells labeled with perfluorocarbon nanoemulsion containing optical nanoparticle.
Figure 8:
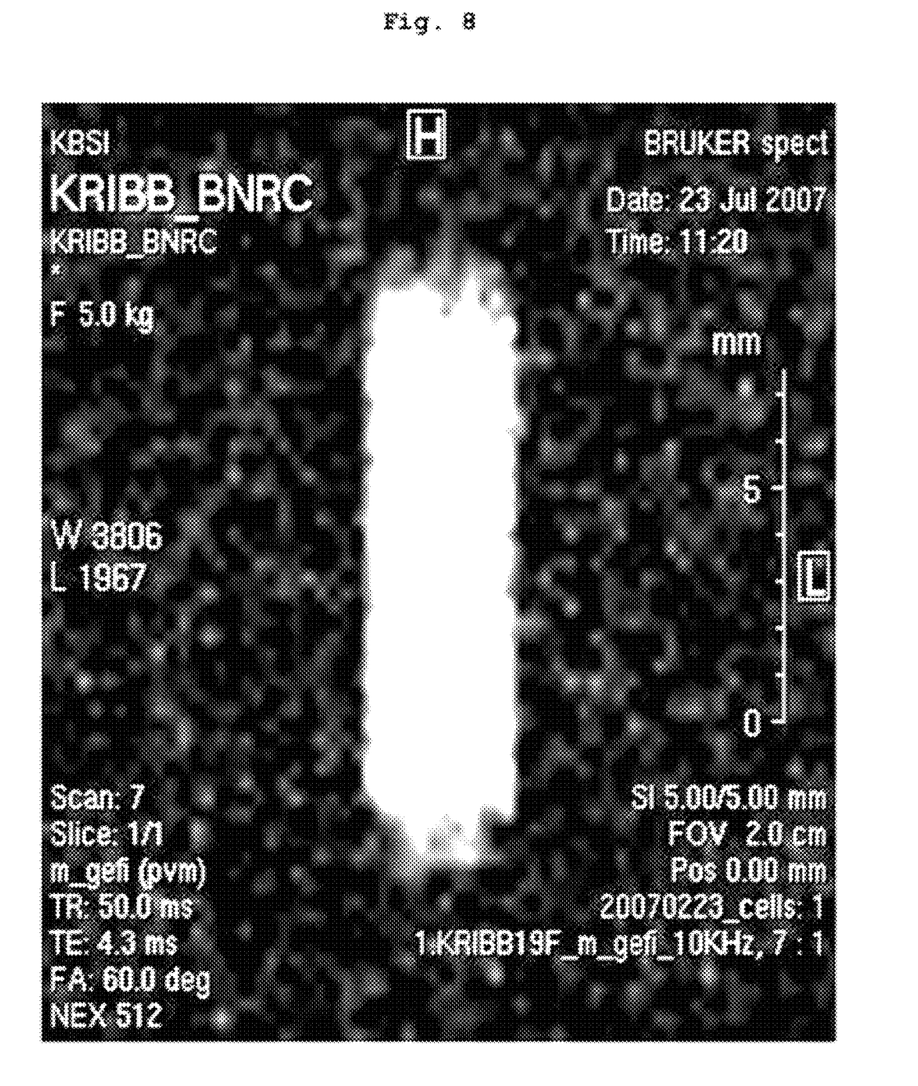
FIG. 8 is a $^{19}$F MRI image of NK cells labeled with perfluorocarbon nanoemulsion containing optical nanoparticle.
Figure 9:
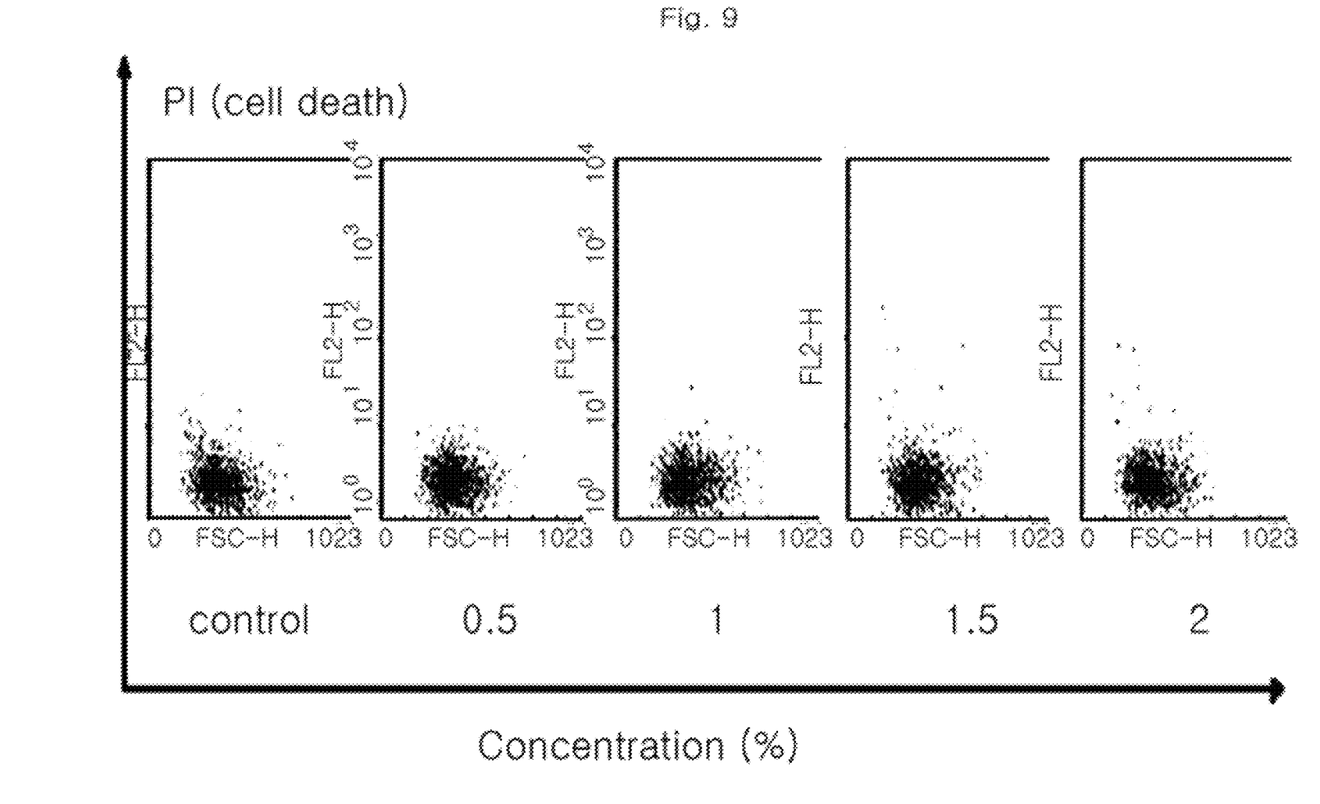
FIG. 9 is fluorescent and $^{19}$F MRI images of macrophage labeled with perfluorocarbon nanoemulsion containing optical nanoparticle.
Figure 10:
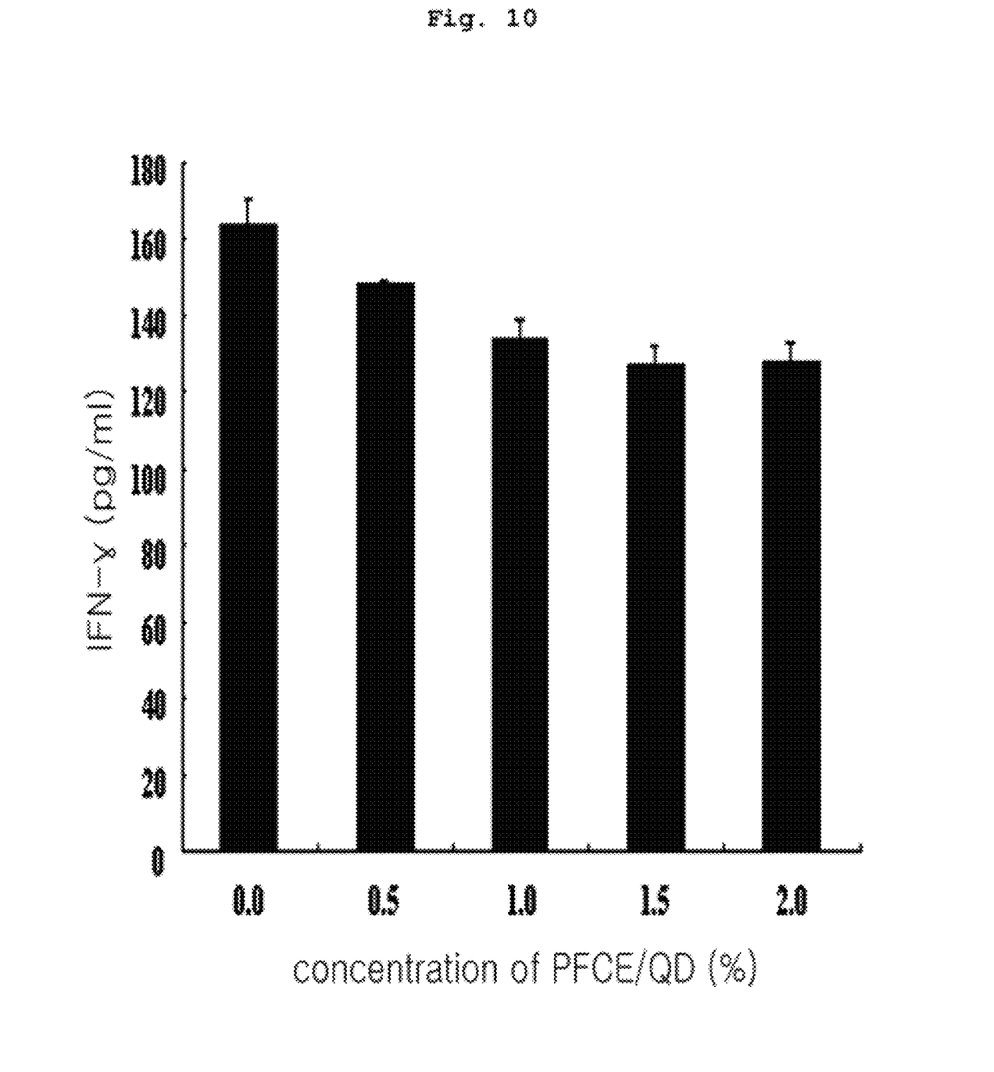
FIG. 10 is fluorescent and $^{19}$F MRI images of dendritic cells labeled with perfluorocarbon nanoemulsion containing optical nanoparticle.

NK cells were plated in the 48-well plate (Falcon, USA) at a concentration of 1×10$^5$/well with α-DMEM complete medium containing 12.5% of fetal bovine serum and 12.5% horse serum. NK cells were treated with 0.5-2% concentration of perfluorocarbon nanoemulsion containing optical nanoparticle, and incubated for 20 hrs at 37° C. under 5% $CO_2$. Cells were harvested and washed twice with 1×PBS. Cells were fixed with 4% paraform aldehyde for 20 min at room temperature, washed twice with 1×PBS then blocked with 1% BSA for 30 min at room temperature. The cells were stained with FITC (Fluorescein isothiocyanate) labeled CD56 antibody (ebioscience, San Diego, Calif.), and stained with DAPI (4,6-diamidino-2-phenylindoledichydrochloride) (Sigma Co. USA) for 10 min before washing with 1×PBS. When the cells were attached on the slide glass by cytospining, the fluorescent mounting medium (Sigma Co, USA) was applied and the slide was covered with a cover slip and microscopically examined. Fluorescent images were obtained using Deltavision RT image system with corresponding filter sets (DAPI, FITC and RD-TR-PE) (FIG. 7). The $^{19}$F MRI image of perfluorocarbon nanoemulsion containing optical nanoparticle was measured using 4.5 T MRI Scanner (Bruker, Germany)(FIG. 8). Results shown in FIGS. 7 and 8 suggested that NK cells were labeled with perfluorocarbon nanoemulsion containing optical nanoparticle. Results also showed that macrophage and dendritic cells were easily labeled with the perfluorocarbon nanoemulsion containing optical nanoparticle according the experimental procedure (FIGS. 9 and 10).

Example 5

Analysis of Cell Viability

The viability of cells labeled with perfluorocarbon nanoemulsion containing optical nanoparticle were analyzed by PI (prodidium idodide) staining method. NK cells were plated in the 48-well plate (Falcon, USA) at a concentration of 1×10$^5$/well with α-DMEM complete medium containing 12.5% of fetal bovine serum and 12.5% horse serum. NK cells were treated with 0.5-2% concentration of perfluorocarbon nanoemulsion containing optical nanoparticle, and then incubated for 20 hrs at 37° C. under 5% $CO_2$. Cell were harvested and washed twice with 1×PBS. Cells were incubated in dark for 15 min after adding 2 μg/ml of PI (Sigma Co., USA). After washing with 1×PBS, the level of PI staining was monitored by FACS (fluorescence activated cell sorter) analysis (Becton Dickinson, Mountain View, Calif.). The result in FIG. 11 showed that there was no significant difference in cell viability when compared with the no emulsion treated control group (FIG. 11).

The perfluorocarbon nanoemulsion containing optical nanoparticle is provided with both optical properties and $^{19}$F magnetic resonance properties, which can be used as a multimodal imaging agent for performing magnetic resonance imaging (MRI) and optical imaging (OI), simultaneously. In addition, the perfluorocarbon nanoemulsion particle containing quantum dot nanoparticle can be applied to various research fields including biological and medical research field that study the molecular images of cells and small animals.

INDUSTRIAL APPLICABILITY

The perfluorocarbon nanoemulsion of the present invention can be used as a multimodal imaging agent for performing magnetic resonance imaging (MRI) and optical imaging (OI), simultaneously. The perfluorocarbon nanoemulsion can be used as a valuable tool in multifunctional and effective cell labeling and cell imaging, and can be applied to various research fields including biological and medical research field that studies the molecular images of cells and small animals.

What is claimed is:

1. A method for labeling and imaging cells comprising:
   contacting the cells with a labeling agent comprising a perfluorocarbon nanoemulsion containing optical quantum dot nanoparticles, a perfluorocarbon continuous phase and lipid liposomes,
   wherein the lipid liposomes encapsulate the optical quantum dot nanoparticles dispersed in the perfluorocarbon continuous phase; and
   imaging the resultant labeled cells,
   wherein, the optical quantum dot nanoparticles are surface reformed by coating the surface of the optical quantum dot nanoparticles with a surface reforming perfluorocarbon
   selected from the group consisting of a perfluorocarbon having a thiol end group, a perfluorinated alcohol phosphate ester and its salt, a perfluorinated sulfonamide alcohol phosphate ester and its salt, a perfluorinated alkyl sulfonamide alkylene quaternary ammonium salt, and a N,N-(carboxyl-substituted lower alkyl) perfluorinated alkyl sulfonamide.

2. The method as set forth in claim 1, wherein the method is performed using cell labeling and imaging reagents alone, or combined with a chemical induction of transfection, or combined with a mechanical induction of transfection.

3. The method as set forth in claim 2, wherein the chemical induction of transfection further comprises supplementation with a cationic agent.

4. The method according to claim 2, wherein the mechanical induction is electroporation or magnetoporation.

5. The method according to claim 1, wherein the optical quantum dot nanoparticles comprise compounds containing two or more elements from Group II-IV or Group III-V in the periodic table.

6. The method according to claim 5, wherein the optical quantum dot nanoparticles are selected from the group consisting of a single core or a core/shell.

7. The method according to claim 1, wherein the perfluorinated alcohol phosphate ester includes a free acid of mono or bis(1H,1H,2H,2H-perfluoroalkyl)phosphate derived diethanolamine salt.

8. The method according to claim 1, wherein the perfluorinated sulfonamide alcohol phosphate ester is one selected from the group consisting of perfluoro-n-octyl-N-ethysulfonamidoethyl phosphate, bis(perfluoro-n-octyl-N-ethylsulfonamidoethyl) phosphate, ammonium salt of bis(perfluoro-n-octyl-N-ethylsulfonamidoethyl) phosphate, bis(perfluorodecyl-N-ethylsulfonamidoethyl phosphate and bis(perfluorohexy-N-ethylsulfonamidoethyl) phosphate.

9. The method according to claim 1, wherein the perfluorocarbon of continuous phase perfluorocarbon is one selected from the group consisting of perfluorotributylamine, perfluorodecalin, perfluoromethyldecalin, perfluorooctylbromide, perfluorotetrahydrofuran, $[(CF_3)_2CFOCF_2(CF_2)_2CF_2OCF(CF_3)_2]$, $[(CF_3)_2CFOCF_2(CF_2)_6CF_2OCF(CF_3)_2]$, perfluoropolymer, perfluorododecane, perfluorobicyclo[4.3.0]nonane, perfluorotritrimethylbicyclohexane, perfluorotripropylamine, perfluoroisopropylcyclohexane, perfluoroendotetrahydrodicyclopentadiene, perfluoroadamantane, perfluoroexotetrahydrodicyclopentadiene, perfluorobicyclo[5.3.0]decane, perfluorotetramethylcyclohexane, perfluoro-1-methyl-4-isopropylcyclohexane, perfluoro-n-butylcyclohexane, perfluorodimethylbicyclo[3.3.1]nonane, perfluoro-1-methyladamantane, perfluoro-1-methyl-4-t-butylcyclohexane, perfluorodecahydroacenapthane, perfluorotrimethylbicyclo[3.3.1]nonane, perfluoro-nundecane, perfluorotetradecahydrophenanthrene, perfluoro-1,3,5,7-tetramethyladamantane, perfluorododecahydrofluorene, perfluoro-1-3-dimethyladamantane, perfluoro-n-octylcyclohexane, perfluoro-7-methyl bicyclo[4.3.0]nonane, perfluoro-p-diisopropylcyclohexane, perfluoro-m-diisopropylcyclohexane, perfluoro-4-methyloctahydroquinolidizine, perfluoro-N-methyldecahydroquinoline, F-methyl-1-oxadecalin, perfluorooctahydroquinolidizine, perfluoro 5,6-dihydro-5-decene, perfluoro-4,5-dihydro-4-octene, perfluorodichlorooctane, perfluorobischlorobutyl ether, perfluorooctane, perfluorodichlorooctane, perfluoro-n-octyl bromide, perfluoroheptane, perfluorodecane, perfluorocyclohexane, perfluoromorpholine, perfluorotripropylamine, perfluorotributylamine, perfluorodimethylcyclohexane, perfluorotrimethylcyclohexane, perfluorodicyclohexyl ether, and perfluoro-n-butyltetrahydrofuran.

10. The method according to claim 1, wherein the lipid liposome has an external layer composed of a lipid or a surfactant.

11. The method according to claim 10, wherein the lipid is selected from the group consisting of natural or synthetic phospholipid, fatty acids, cholesterols, lysolipids, sphingomyelins, tocopherols, glucolipid, stearylarnines, cardiolipins, plasmalogens, lipid with ether or ester linked fatty acids, and polymerized lipids.

12. The method according to claim 10, wherein the surfactant is selected from the group consisting of anionic surfactants, cationic surfactants, nonionic surfactants and amphoteric surfactants.

13. The method according to claim 1, wherein the cell is selected from the group consisting of cancer cells, stem cells, B cells, T cells, NK cells, dendritic cells and phagocytic cells.

* * * * *

UNITED STATES PATENT AND TRADEMARK OFFICE
CERTIFICATE OF CORRECTION

PATENT NO. : 8,697,389 B2  Page 1 of 1
APPLICATION NO. : 12/937875
DATED : April 15, 2014
INVENTOR(S) : Chung et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 452 days.

Signed and Sealed this

Twenty-ninth Day of September, 2015

Michelle K. Lee
*Director of the United States Patent and Trademark Office*